United States Patent
Oostman, Jr. et al.

(10) Patent No.: US 7,129,505 B2
(45) Date of Patent: Oct. 31, 2006

(54) FLUORESCENCE DETECTION INSTRUMENT WITH REFLECTIVE TRANSFER LEGS FOR COLOR DECIMATION

(75) Inventors: Clifford A. Oostman, Jr., Hansville, WA (US); Barry J. Blasenheim, San Jose, CA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 344 days.

(21) Appl. No.: 10/688,131

(22) Filed: Oct. 17, 2003

(65) Prior Publication Data

Related U.S. Application Data

(63) Continuation of application No. 09/941,357, filed on Aug. 28, 2001, now Pat. No. 6,683,314.

(51) Int. Cl.
*G01N 21/64* (2006.01)
(52) U.S. Cl. .................................................. 250/458.1
(58) Field of Classification Search ............. 250/458.1, 250/459.1, 461.1, 461.2
See application file for complete search history.

(56) References Cited

U.S. PATENT DOCUMENTS

| | | | |
|---|---|---|---|
| 4,599,307 A | 7/1986 | Saunders et al. | 435/34 |
| 4,727,020 A | 2/1988 | Recktenwald | 435/6 |
| 4,745,285 A | 5/1988 | Recktenwald et al. | 250/458.1 |
| 5,032,004 A | 7/1991 | Steinle | 350/171 |
| 5,317,162 A | 5/1994 | Pinsky et al. | 250/461.2 |
| 5,483,469 A | 1/1996 | Van den Engh et al. | 364/555 |
| 5,805,346 A | 9/1998 | Tomimatsu | 359/656 |
| 6,097,485 A | 8/2000 | Lievan | 356/338 |
| 6,157,478 A | 12/2000 | Naiki et al. | 359/204 |
| 6,317,207 B1 | 11/2001 | French et al. | 356/317 |
| 6,809,804 B1* | 10/2004 | Yount et al. | 356/73 |
| 2002/0071121 A1* | 6/2002 | Ortyn et al. | 356/419 |

FOREIGN PATENT DOCUMENTS

WO   WO01/27590 A2   4/2001

OTHER PUBLICATIONS

U.S. Appl. No. 09/853,043, filed May 11, 2001, Yount et al.
Becton Dickinson Company paper, "Procount™ Progenitor Cell Enumeration System", 1997, 3 pages.
Becton Dickinson Company paper, "BD LSR System", 1997, 2 pages.

(Continued)

*Primary Examiner*—Constantine Hannaher
(74) *Attorney, Agent, or Firm*—Douglas A. Petry

(57) ABSTRACT

An optical instrument using a plurality of lasers of different colors with parallel, closely spaced beams to stimulate scattering and fluorescence from fluorescent biological particulate matter, including cells and large molecules. A large numerical aperture objective lens collects fluorescent light while maintaining spatial separation of light stimulated by the different sources. The collected light is imaged into a plurality of fibers, one fiber associated with each optical source, which conducts light to a plurality of arrays of detectors, with each array associated with light from one of the fibers and one of the lasers. A detector array has up to ten detectors arranged to separate and measure colors within relatively narrow bands by decimation of light arriving in a fiber. A large number of detectors is mounted in a compact polygonal arrangement by using reflective transfer legs from multiple beam splitters where the transfer legs arise from a polygonal arrangement of beam splitters in a circumference within the circumferential arrangement of detectors.

11 Claims, 11 Drawing Sheets

OTHER PUBLICATIONS

H.M. Shapiro, M.D., "Practical Flow Cytometry", 3rd Ed., 1995, Chapter 1, pp. 1-31.

Steinkamp, J.A., et al, "Improved Method for Multicolor Fluorescence Detection Using Dichroic, Color-Separating Filters", Abstract 431C in, "Abstracts for the XIV International Meeting of the Society for Analytical Cytology", Journal of the Society for Analytical Cytology, Cytometry, Supp. 4 (1990).

* cited by examiner

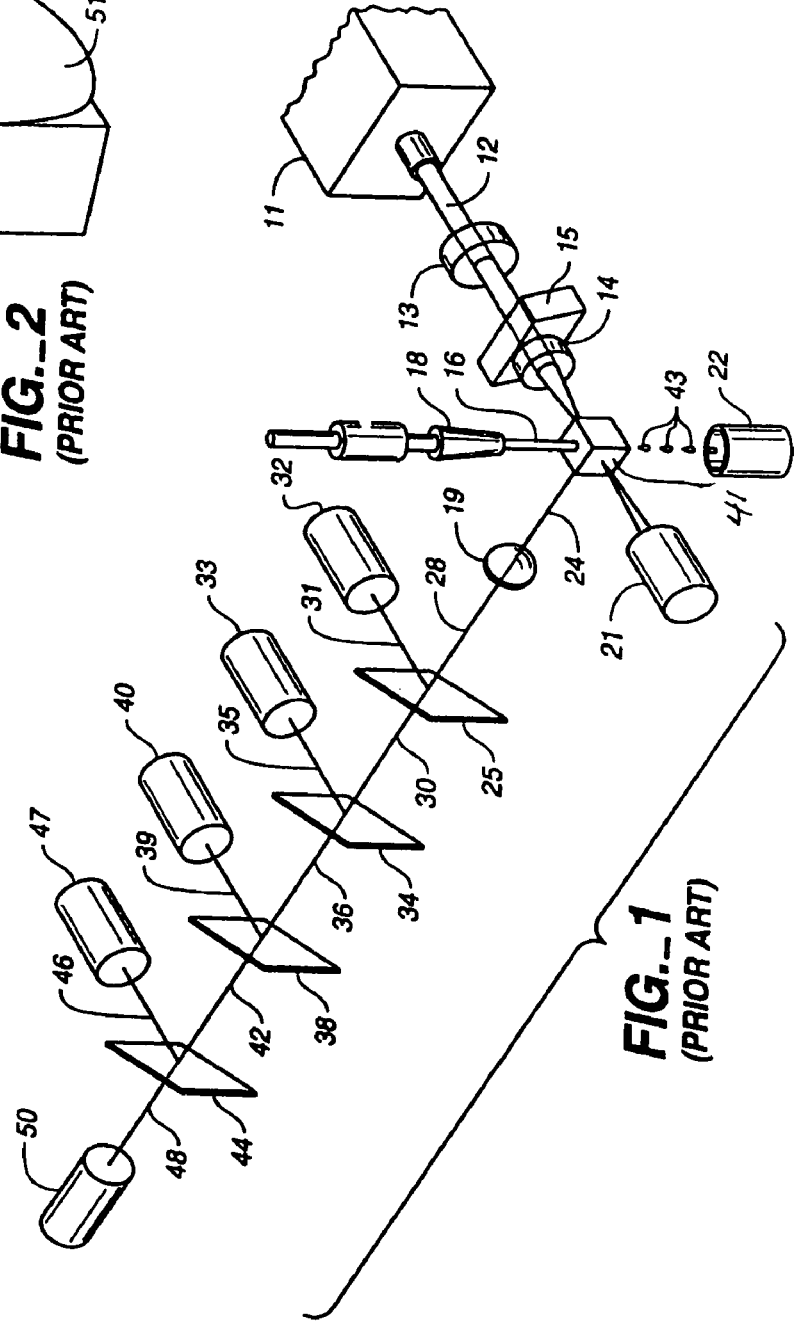
FIG._1 (PRIOR ART)
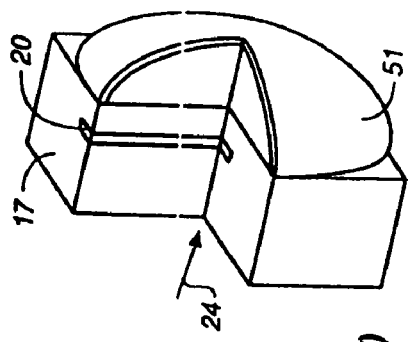
FIG._2 (PRIOR ART)

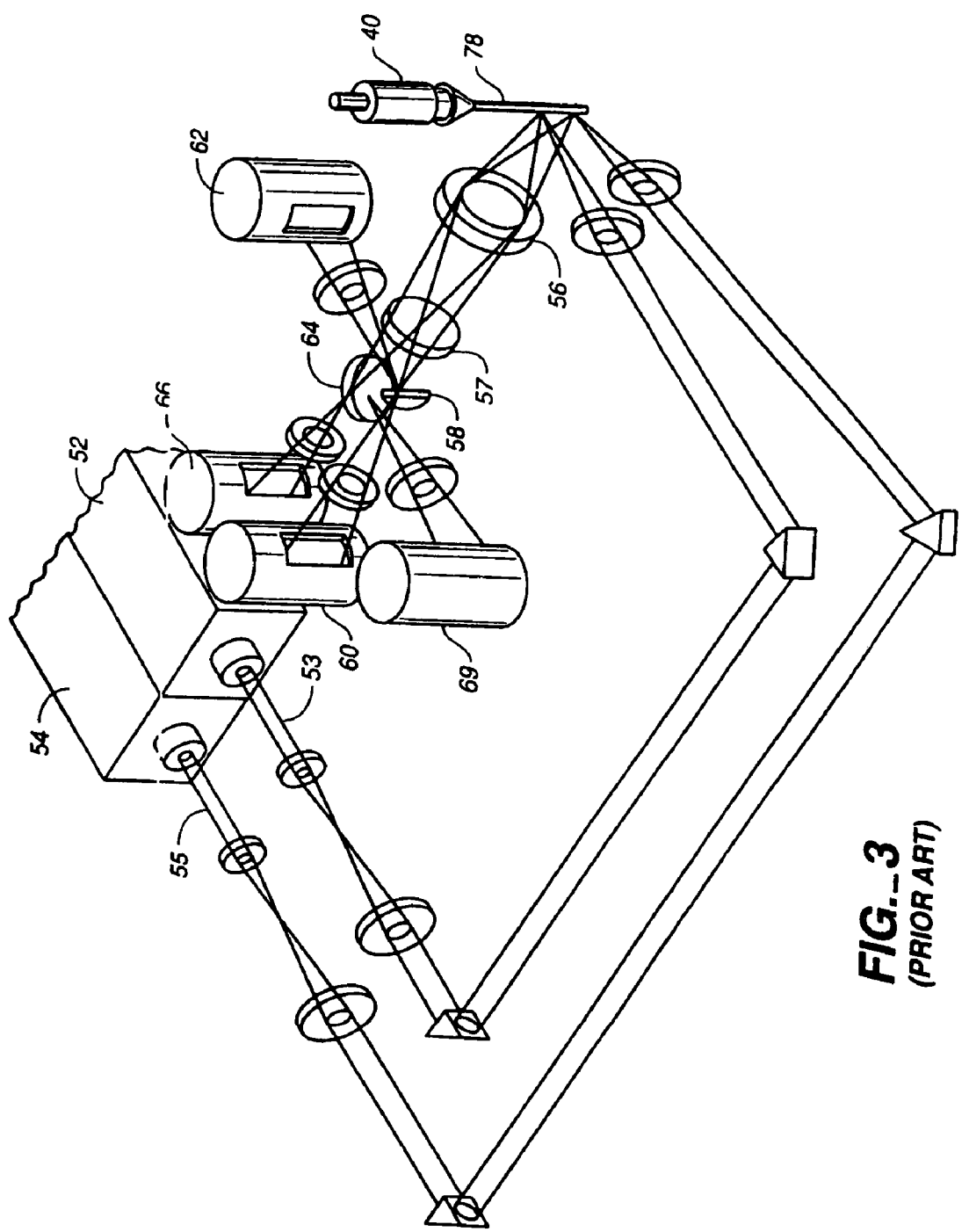
FIG._3
(PRIOR ART)

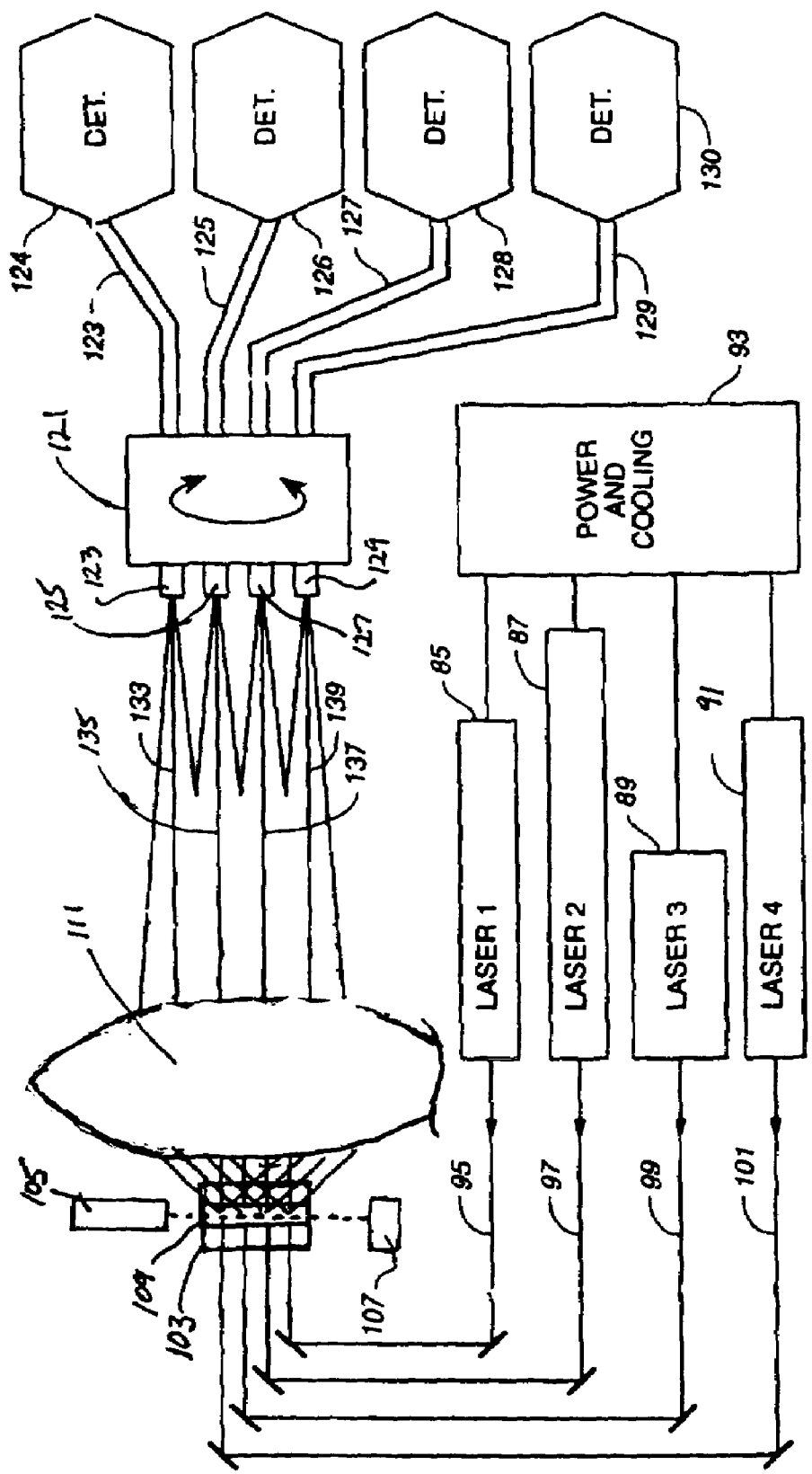
FIG._4

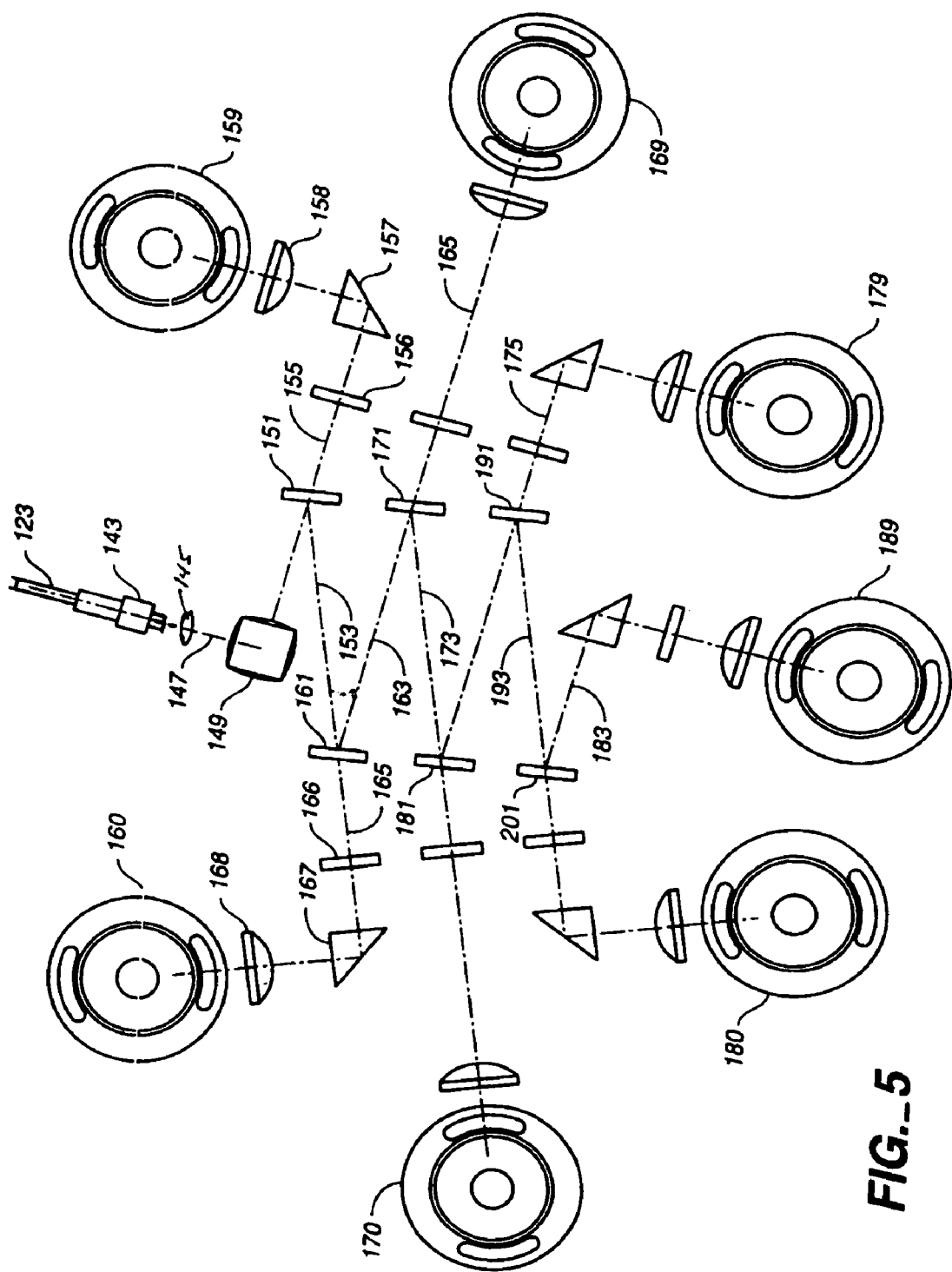
FIG._5

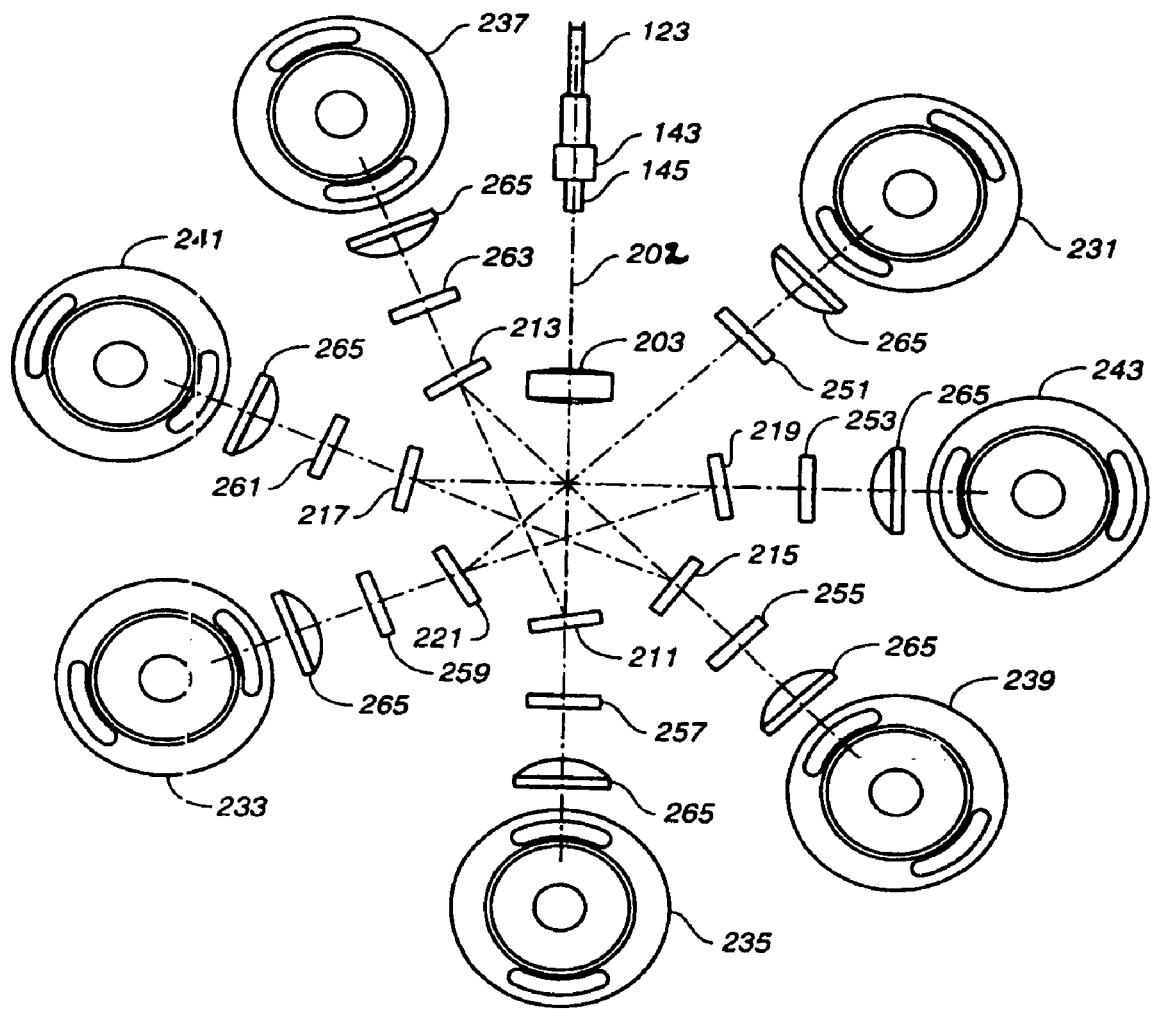
FIG._6

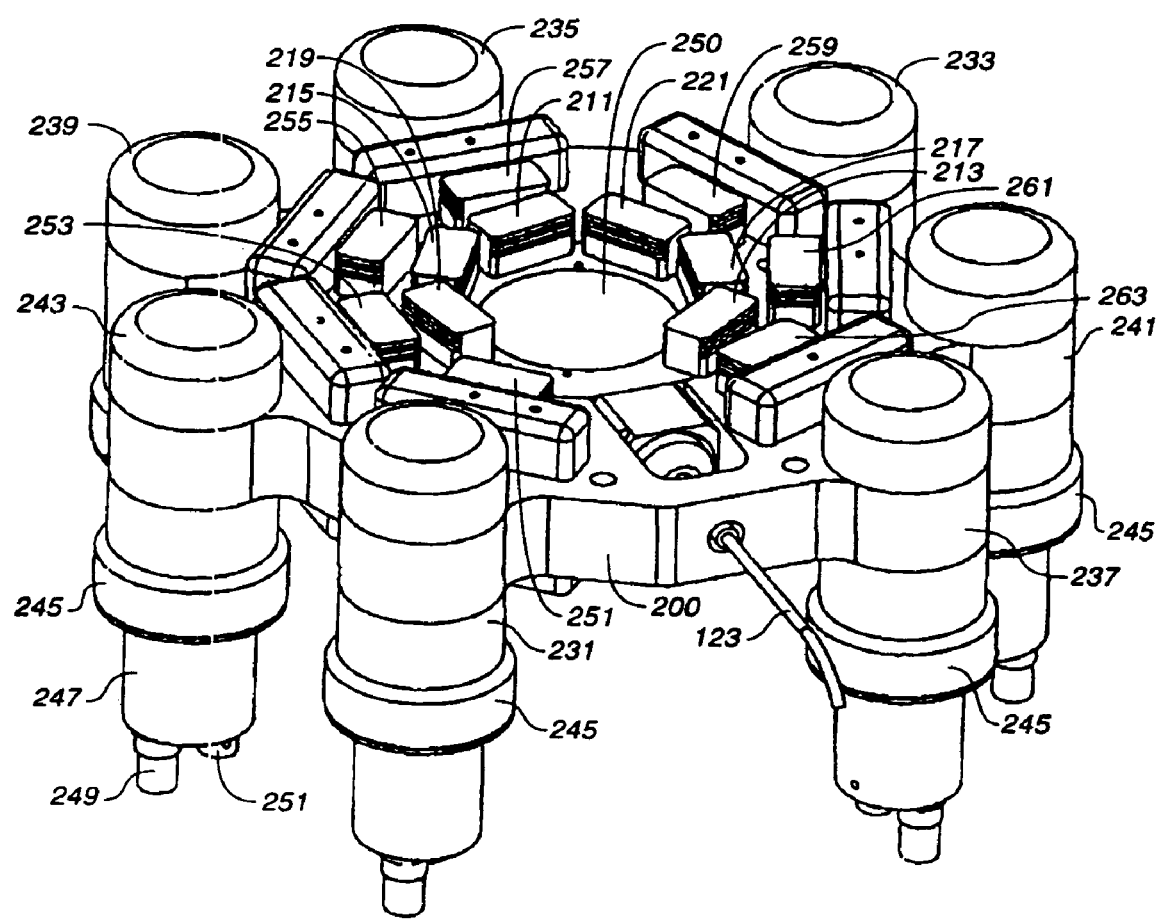
FIG._7

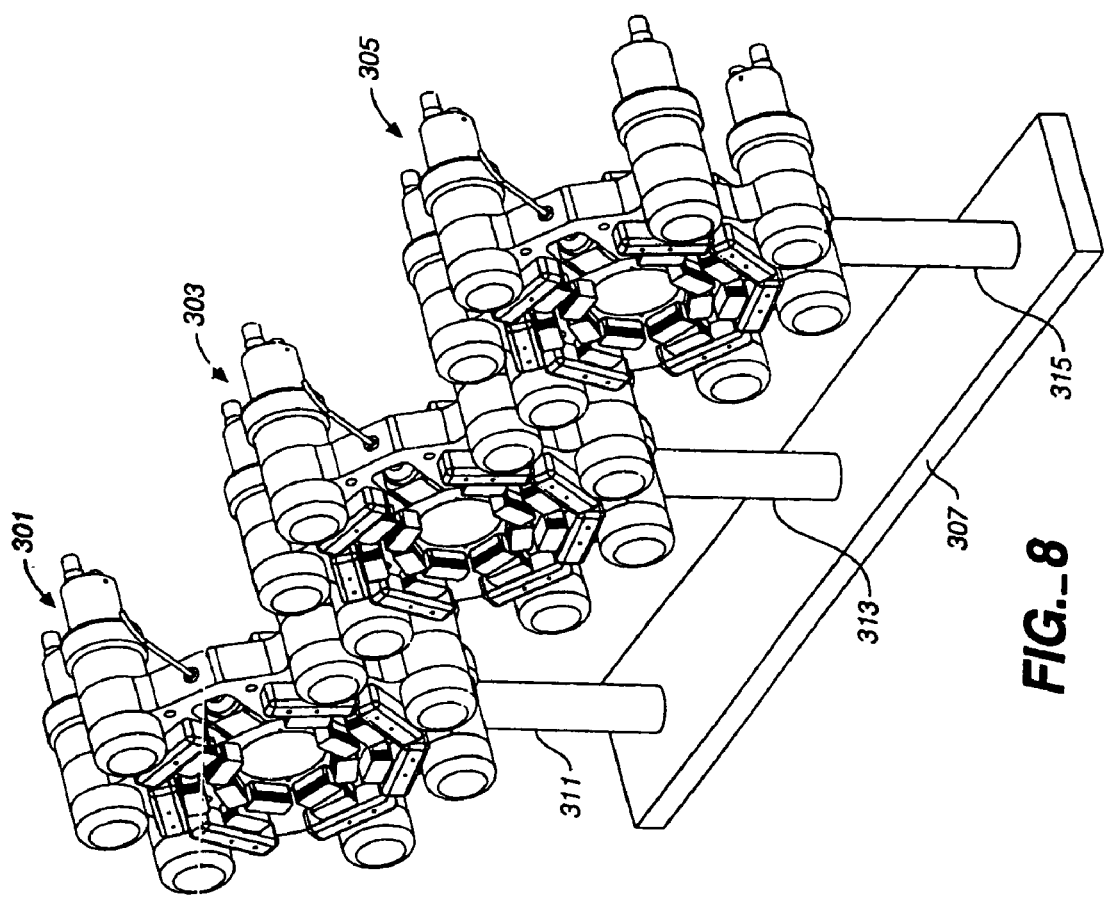
FIG._8

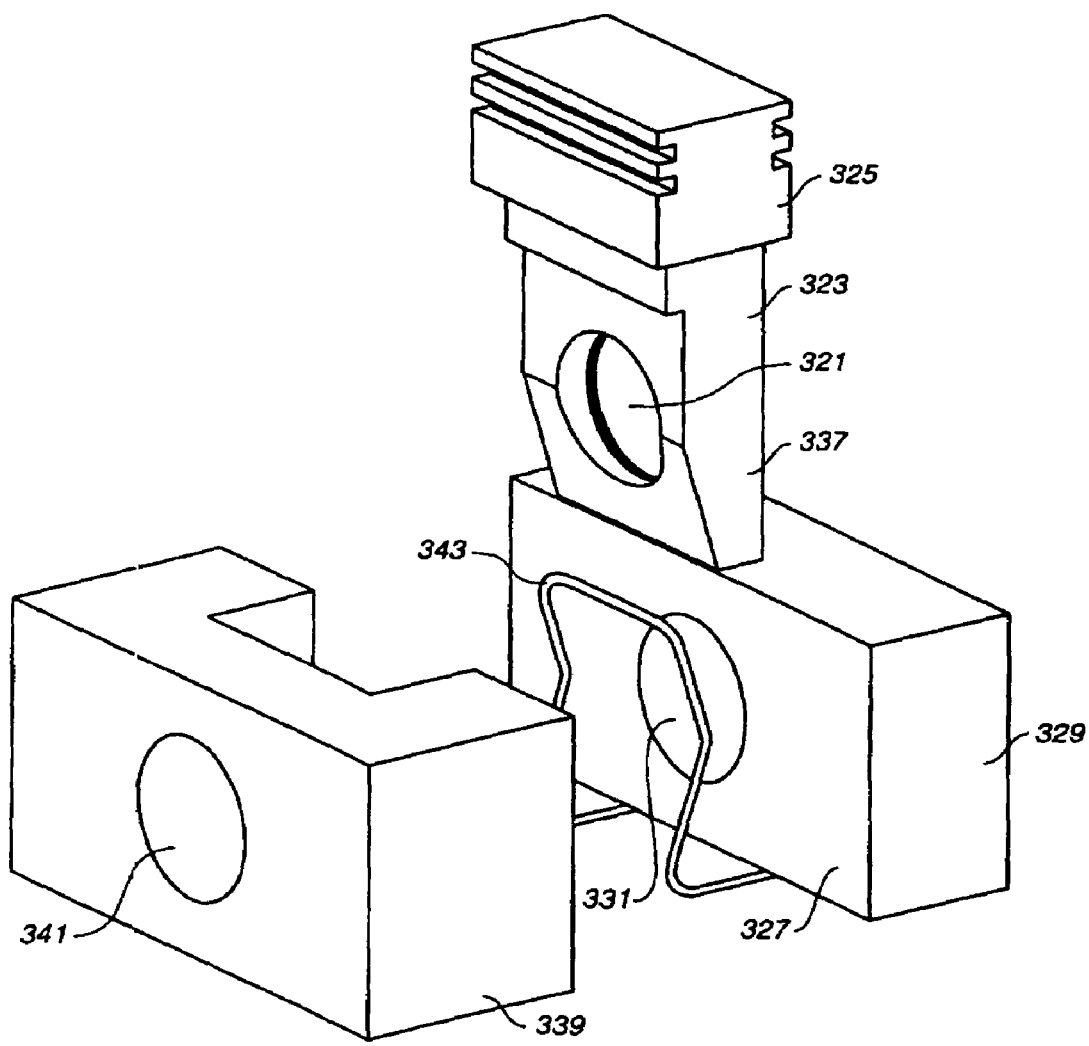
FIG._9

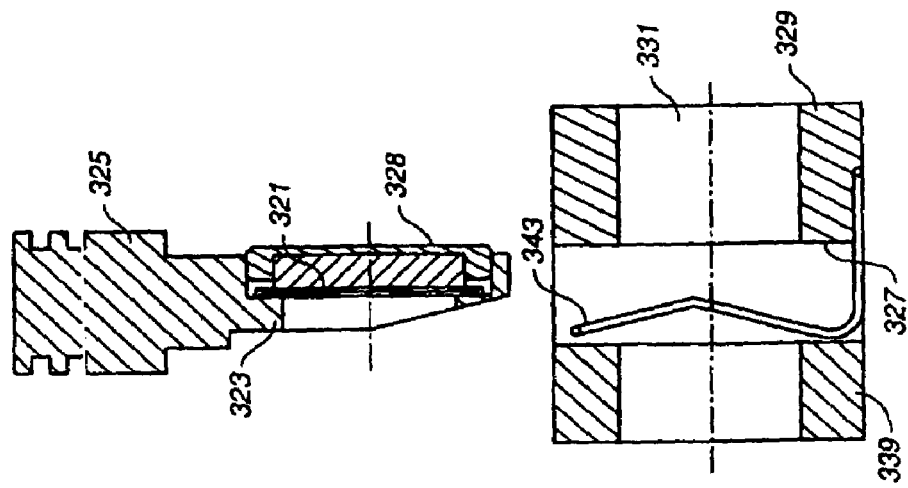
FIG._11
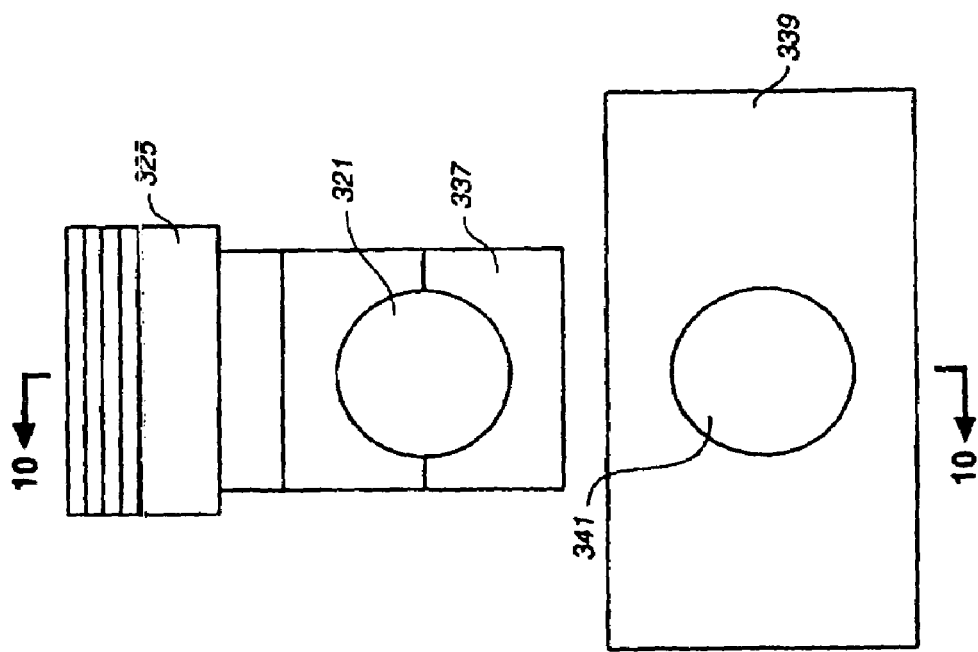
FIG._10

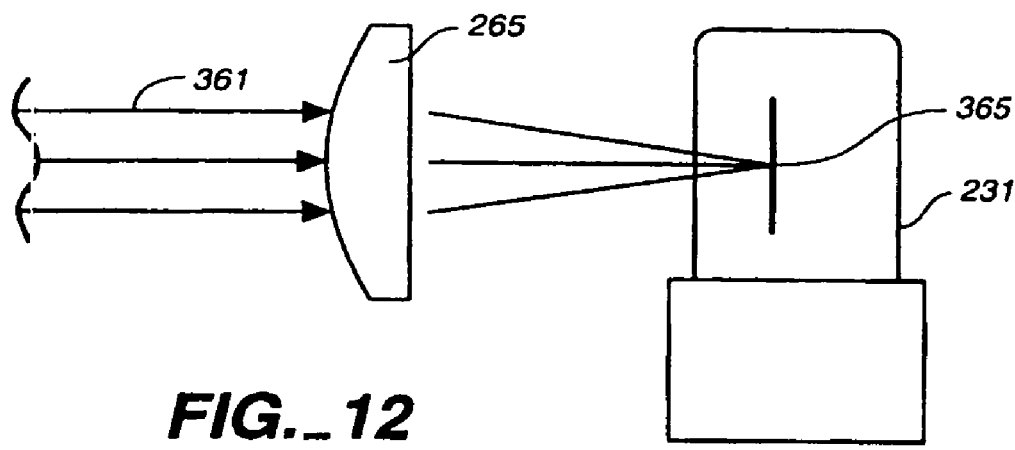
FIG._12
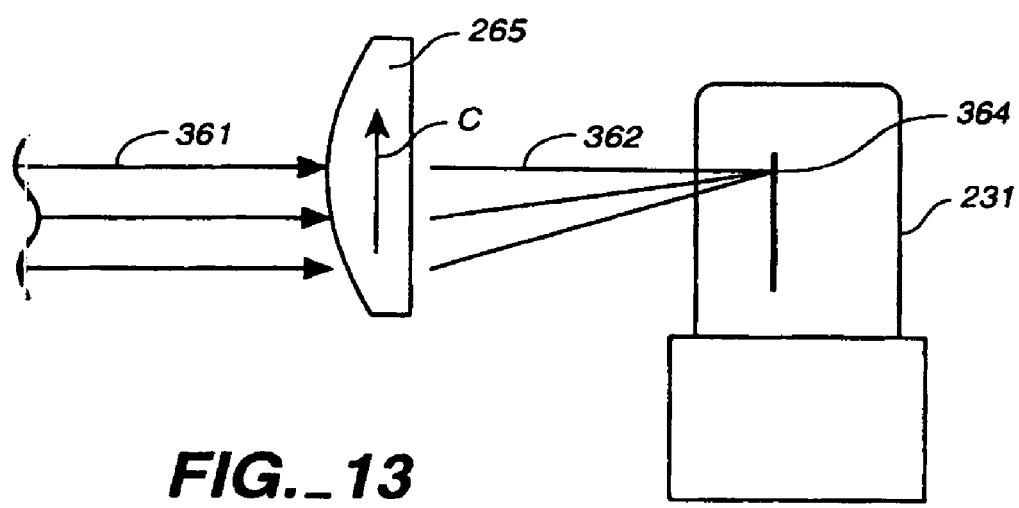
FIG._13
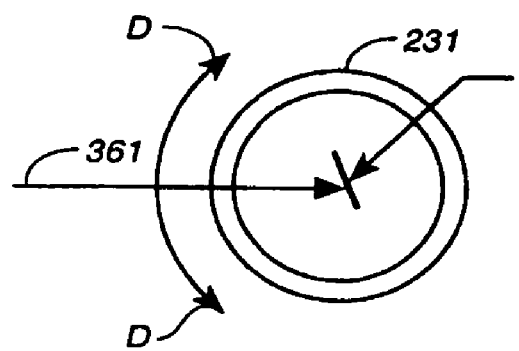
FIG._14

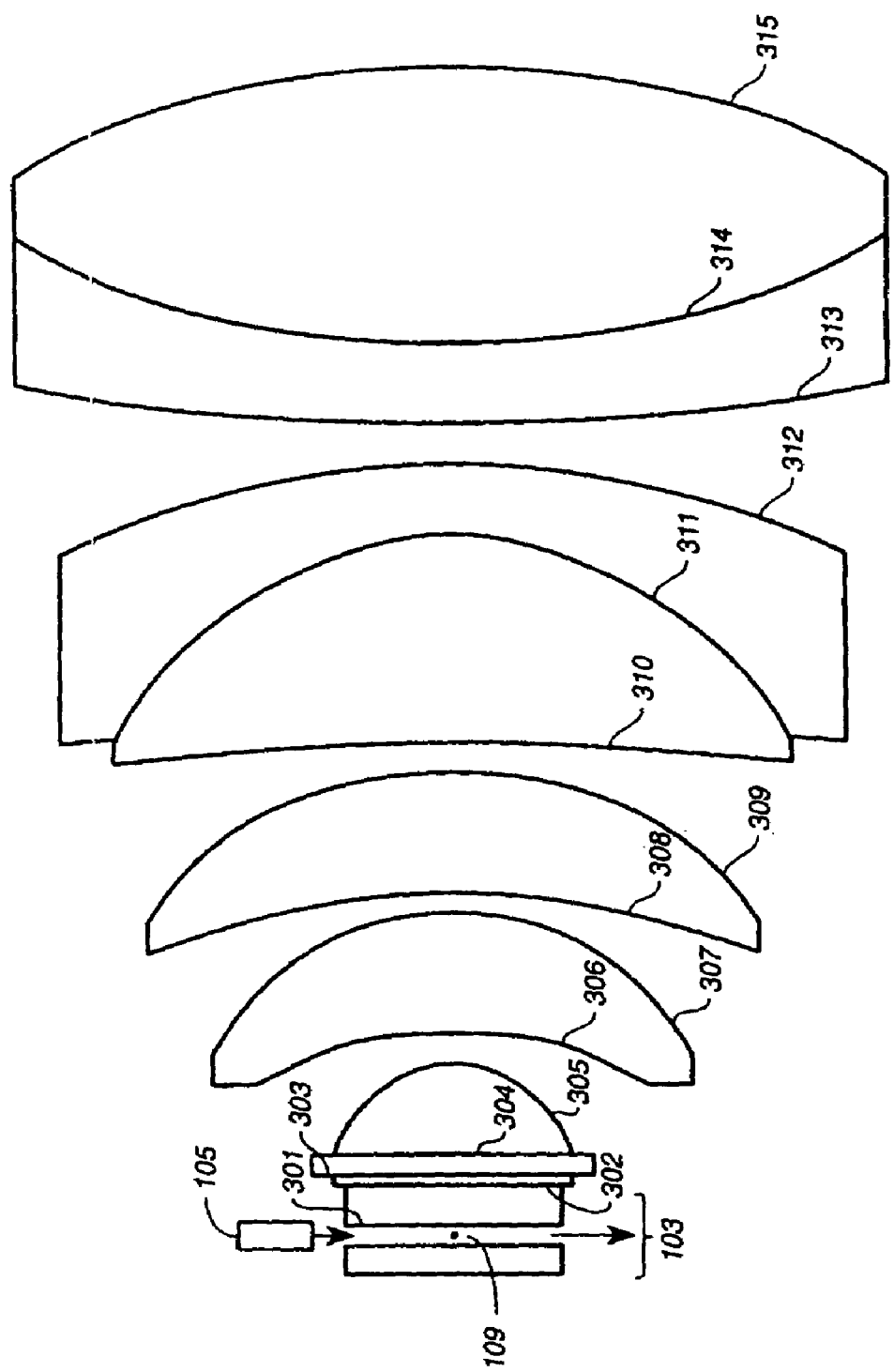
FIG._15

FLUORESCENCE DETECTION INSTRUMENT WITH REFLECTIVE TRANSFER LEGS FOR COLOR DECIMATION

The present application is a continuation of U.S. Ser. No. 09/941,357, filed Aug. 28, 2001, which issued on Jan. 27, 2004, as U.S. Pat. No. 6,683,314.

TECHNICAL FIELD

The invention relates to analytical instruments for flourescent light analysis from target specimens and, more particularly, to such an instrument employing increased color decomposition of fluorescent signals from target substances.

BACKGROUND ART

As an example of fluorescent light decomposition for bioanalytical studies, in high throughput screening, the ability to simultaneously detect a plurality of fluorescent dyes with good wavelength discrimination enables deeper multiplexing and higher throughput. In another example using fluorescent light analysis, simultaneous detection of multiple dyes associated with cells allows simultaneous assay of cell surface antigens, organelle states, nucleic acid assay, and intercellular protein content to be detected in a single assay. Multiple wavelength detection requires detectors which can separate many bands of colors. This has commonly been done using dichroic mirror beam splitters.

U.S. Pat. No. 5,317,162 to B. Pinsky and R. Hoffman, assigned to the assignee of the present invention, describes an instrument for phase resolved fluorescent analysis. The architecture of that instrument is similar to prior art instruments which rely upon color decomposition of a beam of fluorescent light derived from a laser impinging upon a fluorescent target. Such an apparatus is described in the book *Practical Flow Cytometry*, by H. M. Shapiro, Third Edition (1995), p. 9. The book describes an apparatus similar to what is shown in FIG. 1. A laser beam 12 from an air cooled argon ion laser 11 is used to generate a fluorescent signal which is subsequently decomposed or decimated. The beam 12 passes through focusing elements 13, 14 and 15 to impinge upon a fluorescent substance in a flow cell 41. Fluorescent target material, such as fluorescently tagged cells or particles within a liquid stream 16 flow through the flow cell 41. Particles 43 having passed through flow cell 41 are collected in container 22. Flow is adjusted by a fluidic system 18 which provides a hydrodynamically focused flow of cells within a sheath fluid. As the target substance passes through the flow cell, the focused light beam 12 intersects the liquid stream, causing fluorescent excitation, including the scattering of light. A photodiode detector 21 is positioned to receive forwardly scattered light. The fluorescent light is typically collected at an angle which is 90° relative to the excitation access of the light beam 12. Axis 24 represents the 90° viewing axis for collection of fluorescent light. Objective lens 19 is placed across axis 24 to collect and collimate the fluorescent signal from the target substance. Fluorescent light collected by the lens 19 is formed into a beam 28 which impinges upon the dichroic mirror 25. The dichroic mirror reflects light above 640 nm and transmits the remainder as the transmitted leg 30. Reflected leg 31 is directed to the red light fluorescence detector photo multiplier tube (PMT) having a 660 nm longpass filter. Detector 32 thus registers the red light component of the collected fluorescent signal from the flow cell 41. The transmitted leg 30 impinges upon the dichroic mirror 34 which reflects light above 600 nm. The reflected leg 35 is orange light which is detected by the orange fluorescence detector PMT 33 having a 620 nm bandpass filter. The transmitted leg 36 impinges upon the dichroic mirror 38 which reflects light above 550 nm and transmits the remainder in transmitted leg 42. Reflected leg 39 is detected by the yellow fluorescence detector PMT 40 having a 575 nm bandpass filter.

The transmitted leg 42 impinges upon dichroic mirror 44 which reflects light above 500 nm. The reflected leg 46 impinges upon the green fluorescence detector PMT 47, while the transmitted leg 48 consists of essentially blue light which is directed into the orthogonal scatter detector PMT 50 with a 488 nm bandpass filter, registering blue light. In this manner, the fluorescent signal in beam 28 collected by collector lens 19 is decomposed into five colors with the amplitude of each detector being recorded simultaneously to form a spectral characteristic of the fluorescent material illuminated by the laser beam.

The flow cell 41 is typically a flat-sided quartz cuvet of square or rectangular cross-section with a flow path therethrough. Such a quartz cuvet of the prior art is described in international patent publication WO 01/27590 A2, owned by the assignee of the present invention, shown in FIG. 2.

In that international patent application, the flow cell mentioned above is described with an aspheric reflective light collector, unlike the lens 19 shown in FIG. 1. The apparatus of the international patent application mentioned above is shown in FIG. 2 where a flow cell 17 is a quartz block having a flow channel 20 where a liquid stream containing fluorescent material is directed through the cell in a stream controlled by a nozzle. The flow cell of FIG. 2 has a reflective aspheric light collector 51 collecting light scattered to a side of the flow cell opposite the side where lens 19 is situated. An aspheric reflective element 51, placed on the side of flow cell 17 opposite collector 19 serves to augment the light directed toward lens 19, or in some cases performs the function of lens 19. The reflective collector 51 is coated with a broadband reflecting material for augmenting the amount of light collected from the flow cell. The aspheric shape may be parabolic or ellipsoidal, having focal properties to match light collector 19 of FIG. 1.

The apparatus of FIG. 3 is described in U.S. Pat. No. 4,727,020 to D. Recktenwald and assigned to the assignee of the present invention. This device shows a pair of lasers 52 and 54 directing light to a flow cell 78 so that two different illumination profiles may be used to illuminate a sample. Each laser is selected for stimulating the desired fluorescent emission from target substances. A set of detectors is associated with a different color band. For example, laser 52 generates a beam 53 impinging upon the flow stream 78 and producing a fluorescent signal collected by lens 56, focused by lens 57 onto dichroic mirror 58, a beam splitter, for analysis by detectors 60 and 62. Similarly, laser 54 generates a beam 55 which impinges upon the flow which includes the particles under study in air and generates scattered fluorescent light, collected by light collector 56 and imaged by lens 57 onto dichroic mirror 64 where the beam is split between detectors 66 and 69. In summary, it is known that groups of detectors can be associated with different lasers simultaneously illuminating the same target substance.

An object of the invention was to provide an improved system for detecting fluorescent light having multiple colors emitted from a target using a greater number of detectors than has been achieved in the prior art.

SUMMARY OF THE INVENTION

The above object has been achieved in an optical instrument having a detector arrangement featuring a larger number of spectrally diverse detectors than previously available. The detectors are fed by a plurality of lasers of different colors with parallel, spaced apart beams impinging upon fluorescent target material at different locations which may be in a channel, a plate, or the like. By using a plurality of lasers, a wide range of spectral responses may be stimulated from fluorescent target material. The target material may be fixed or flowing. Spatially separated fluorescence associated with each beam and emanating from the target material is collected by a large numerical aperture collector lens that preserves the spatial separation of the light originating from the plurality of sources, i.e. the fluorescent signatures of the laser beams on the target material is preserved. Fluorescent light stimulated by the different sources is imaged into a plurality of optical fibers that carry the light to separate detector arrays. Each array has a series of beam splitters in a series or cascade arrangement receiving light from an associated fiber and relaying part of the light to a downstream beam splitter, spectrally filtering the light on each relay within the cascade arrangement by means of coatings associated with the splitters. Within each array, light reflected from a beam splitter is forwarded to a downstream splitter, while light transmitted through a beam splitter is sent to a detector. This means that the reflected component is a broadband wavelength component and the transmitted component is filtered to be a narrowband wavelength component. For the last beam splitter, light from the reflective leg may be sent to a detector, as well as light from the transmitted leg. Since, for most optical coatings on a beam splitter, the fraction of light reflected from a beam splitter exceeds the transmitted fraction, the downstream beam splitters receive more light from the reflective transfer legs than the prior art arrangement where downstream beam splitters receive light from the transmitted transfer leg. Each array of detectors is arranged in a polygonal compact cluster. The detector configuration of the present invention is modular because light from each laser is spatially separated from other lasers and each detector cluster has at least 6 detectors. The clusters may be physically separated since optical fibers can feed light to clusters in remote locations or in stacks or racks. In this instrument, collected light is transmitted to a plurality of beam splitters. Note that the beam splitters, split light into a transfer leg and a transmitted detector leg, as in the prior art. However, unlike the prior art, the transfer leg is reflected from beam splitters and forwarded to another beam splitter and the transmitted detector leg is directed to a detector. This is true for a majority of beam splitters, but not for the last one receiving a maximally attenuated transfer leg where the transfer leg is either sent to a detector or terminated. So the last dichroic mirror may be associated with two detectors, one for the reflected leg and one for the transmitted leg. By using reflective transfer legs for most detectors, the detectors may be clustered in a polygonal arrangement of between five and ten light detectors in a common plane. Here, the term "most detectors" refers to all transfer legs except the last one, but is not limited to the last leg.

By maintaining spatial separation for the input beams, spatial separation can be preserved in the output transfer beams, with each transfer beam directed into an optical fiber for delivery to a detector cluster. This allows detector clusters to be stacked or placed in racks, with optical fibers carrying transfer beams to the location of an input port of each cluster. Once inside of a cluster, the transfer beam is decimated by the dichroic beam splitters, each beam splitter inclined to a transfer leg at a preferred angle centered on 11.25 degrees. Other angles will work but not as efficiently. Each beam splitter achieves color separation in the usual way, i.e. by transmitting light of a particular wavelength. This transmitted light is directed to a photomultiplier tube, or the like, which is positioned, to the extent possible, to detect light in the transmitted detector legs associated with the split beam. A focusing lens and the detector photomultiplier tubes are positionally relatively adjustable so that an optimum detector position can be found by motion of a detector element relative to a lens focusing incoming light. In this manner, the fluorescence associated with each of several laser beams is simultaneously decimated into bands characteristic of the target material within the detector array of each cluster. A group of clusters provides color decimation much greater than heretofore available. Moreover, the apparatus is modular because a greater number of fibers can feed a greater number of clusters. One of the advantages of using a reflective transfer leg to relay the optical signal for decimation, rather than the transmitted leg, is that the reflective transfer leg is a stronger optical signal. After encounters with several beam splitters, the signal attenuation in a relayed reflective transfer leg signal is substantially greater than for an optical signal in which the relay was transmitted through an equal number of beam splitters, as in the prior art.

In one embodiment, the light collection and detection optics are included in a system having a plurality of lasers producing input beams of different wavelength profiles to simultaneously illuminate a fluorescent target, usually fluorescent particulate matter which could be discrete small particles, including cells, or large biological molecules. The term "color decimation" refers to the simultaneous spectral breakdown of polychromatic light beams from a target substance into narrow bands of light arriving at detectors. Scattered light is measured by other detectors not relevant to this invention or this application. Scatter detectors are not described herein. Collection of fluorescent light is by a lens similar to a microscope immersion lens of large numerical aperture, the lens forming output transfer beams directed to a plurality of dichroic mirrors. After collection, the light is imaged into fibers, then distributed to "n" clusters of "m" detectors, yielding an "n" times "m" number of detectors resolving the fluorescent light stimulated by the input beams. Each cluster isolates light within the corresponding array of detectors. Clusters may be mounted on rails, racks or stacks in a modular arrangement.

DESCRIPTION OF THE DRAWINGS

FIG. 1 is a perspective plan view of a multi-color flow cytometer with single wavelength excitation in accordance with the prior art.

FIG. 2 is a perspective view of a light collector of the prior art for use with a flow cytometer of the kind illustrated in FIG. 1.

FIG. 3 is a perspective view of a multi-color flow cytometer with plural wavelength excitation and a polygonal arrangement of detectors in accordance with the prior art.

FIG. 4 is a plan view of a multi-color optical instrument of the present invention.

FIG. 5 is a top plan of a planar polygonal detector arrangement showing decimation of an incoming beam with reflective transfer leg beam splitters in accordance with the present invention, the incoming beam received from a fiber bundle illustrated in FIG. 4.

FIG. 6 is a top plan of an alternate planar polygonal detector arrangement showing decimation of an incoming beam with reflective transfer leg beam splitters, as in FIG. 5 but with the beam having a folded path for compact placement of the detectors.

FIG. 7 is a perspective assembly view of the apparatus of FIG. 6.

FIG. 8 is a perspective plan view of three detector arrays of the kind shown in FIG. 7 mounted on a rack in accordance with the present invention.

FIG. 9 is a perspective plan view of a detail of a mirror holder used in the apparatus of FIG. 7.

FIG. 10 is a front elevation of the mirror holder illustrated in FIG. 9.

FIG. 11 is a side sectional view of the mirror holder of FIG. 10, taken along lines 10—10.

FIG. 12 is a side plan view of a detector photomultiplier tube and optics used in the detector arrangements shown in FIGS. 5 and 6.

FIG. 13 is a side plan view of a motion to optimize the sensitivity of the detector shown in FIG. 12.

FIG. 14 is a top plan view of a motion to optimize the sensitivity of the detector shown in FIG. 13.

FIG. 15 is a plan view of a light collector lens for use in the instrument input end arrangement illustrated in FIG. 4.

BEST MODE FOR CARRYING OUT THE INVENTION

With reference to FIG. 4, a first laser 85, a second laser 87, a third laser 89, and a fourth laser 91, all produce light with unique wavelength profiles and all are connected to respective power supplies and a cooling module 93. The lasers emit respective beams 95, 97, 99 and 101 which are directed by means of beam-turning mirrors toward flow stream 103 causing the beams to intersect with the stream. Although the preferred embodiment features a flow cytometer, this instrument is merely illustrative of instruments which employ fluorescence detection and color separation. Other instruments include microscopes, electrophoresis instruments, spectrophotometers, and the like. The scope of the present invention is therefore not limited to flow cytometers.

A fluidic system 105 feeds tagged target liquid substances into a stream 103 in a controlled manner. Material which passes through the beam illuminated zone is collected in collection cup 107. The illuminated zone is established by the four laser beams that impinge upon fluid tagged target material, thereby causing scattering and fluorescence. Each beam has a characteristic color produced by different types of lasing material. For example, characteristic laser illumination wavelength profiles may be produced by $CO_2$ lasers, argon ion lasers, copper vapor lasers, and helium neon lasers. Other colors are available from different types of lasers. The output power of each laser is typically between 10 and 90 milliwatts. At such power levels, a sufficiently strong optical signal is produced without damaging coatings on the surfaces of mirrors, fibers or beam splitters. Coatings are selected to achieve desired passband transmissions and may be specified from coating manufacturers.

Light of different colors intersects the flow stream 103 and interacts with fluid sample causing scattering and fluorescence that is spatially separated along a line parallel to the flow channel 109. Scattered light can be processed by well-known scatter detectors. For simplicity, this description deals only with fluorescent light. This light appears to be originating at four spaced apart point sources or spots, each of which is imaged by a lens light collector 111 to four respective optical fibers 123, 125, 127 and 129, all held in place by a movable holder 121 which securely mounts the fibers and allows both rotational and axial adjustment of the fibers relative to light collector 111. In other words, the holder 121 may be moved so that the fibers optimize the input light into the fibers from collector 111. The focal spots produced by collector 111 enter the tip of each respective fiber 123, 125, 127 and 129, each of which is a multi-mode fiber.

Light collector 111 is a group of lens elements which is described with reference to FIG. 15. The collector is placed very close to the flow stream, within a few millimeters. The distances shown in FIG. 4 are not to any scale and are out of proportion. This collector gathers fluorescent light from the fluorescent target material. The collector lens is a microscope objective lens similar to the fluid emersion microscope objective lens shown in U.S. Pat. No. 5,805,346, except that the lens of the present invention is a positive meniscus lens, while the fluid emersion microscope objective lens of the '346 patent is a negative meniscus lens. Other differences exists, but the lenses are similar in the number of optical elements and their arrangements. Various supports may be used with the goal of reducing vibration and allowing proper alignment of optical elements along the optical axes 133, 135, 137, and 139 defined by collector 111. The optical axes are maintained by each of the fibers, although each of the fibers may be bent to remove light to the location of a detector array. Light in each of the fibers 123, 125, 127 and 129 is transmitted to a respective detector cluster 124, 126, 128 and 130 which houses an array of detectors. Each array processes fluorescent light which has maintained spatial separation, i.e. color independence, to a large extent. In other words, the fluorescence stimulated by a particular laser has been preserved and forwarded to an array of detectors which operates independently from other arrays of detectors. Each array of detectors differentially separates bands of light by filtering, using coatings on beam splitters and lenses, in a known manner. With each cluster having between 3–4 and 10 or more detectors, each detector receiving a passband of between 10 and 75 nanometers, the instrument of the present invention has a wide spectral response.

Details of a detector array or cluster are shown in FIG. 5. The optical fiber 123 has a fiber terminal 143, which allow emergence of light and formation of a beam by means of a collimating lens 145. The output beam 147 is directed toward a beam-turning mirror 149 directing light at a first beam splitting element 151 which is a dichroic mirror transmitting light in beam 155 in a transmitted detector leg toward a filter 156, a beam-turning element 157, and a focusing element 158 which directs the beam onto a light sensitive element of a photomultiplier tube 159. The tube is adjusted so that its most sensitive area is exposed to the incoming beam. This beam is known as the transmitted detector leg because it is transmitted through the beam splitting element 151. The beam splitting element has a coating which allows transmission of one band of optical signals, while reflecting light in another band in the form of beam 153 which forms a reflective transfer leg for the light which was originally in beam 147. The reflective transfer leg 153 is seen to fall upon another beam splitting element 161 which is a dichroic mirror having different optical characteristics from the beam splitter 151. The colors removed by beam splitter 161, as well as the other beam splitters, are different, each beam splitter removing a selected band of colored light in the same manner, but different wavelengths, as in beam splitters of the prior art described with reference to FIG. 1.

Beam splitter 161 has a reflective transfer leg 163 reflected from the surface of the splitter, as well as a transmitted detector leg 165 transmitted through the beam splitter to the filtering element 166, the beam-turning element 167 and the focusing element 168. The transmitted beam impinges upon a sensitive portion of detector 160 where the amount of light associated with the band transmitted by beam splitter 161 is measured. In the same manner, beam splitters 171, 181, 191 and 201 split incoming beams which are light beams reflected from upstream beam splitters, with beam splitter 191 being upstream of beam splitter 201, beam splitter 181 being upstream from beam splitter 191, and beam splitter 171 being upstream from beam splitter 181, etc. Each beam splitter, except for the last one, beam splitter 201, separates light into a reflective transfer beam, with the transfer beam 173 being reflected from beam splitting dichroic mirror 171 and the transmitted beam through dichroic mirror 171 being beam 165 impinging upon detector 169. On the other hand, the reflected beam 173 is transmitted to beam splitter 181, with the transmitted leg being directed to detector 170. Beam 175, passing through the beam splitter 191, is directed to a detector 179 while the reflected leg 193 goes to the last beam splitter, namely dichroic mirror 201. This element, unlike the other beam splitters, has two detectors associated with it. One detector 180, receives light transmitted through the beam splitter 201 toward detector 180 while light reflected from beam splitter 201 forms a reflected leg 183 which impinges upon detector 189. In this manner, all of the detectors illustrated in FIG. 5 form an array which decimates light from a single fiber 123. As mentioned previously, the fiber 123 is associated with scattered and reflected light collected from one of the lasers mounted on the optical bench. Thus, for each laser there is an array of detectors in a cluster. In FIG. 5, the transfer leg forwarded upstream from one beam splitter to the next follows a zigzag pattern. In FIG. 6, the transfer legs intersect in a star-shaped pattern yielding a more compact polygonal arrangement of detectors.

In FIG. 6, the optical fiber 123 is terminated in a terminal 143 directing an output beam 202 through a collimating lens 203 and thence onto an array of beam splitters 211, thence to beam splitter 213, then to beam splitter 215, then to beam splitter 217, then to beam splitter 219, and, lastly, to beam splitter 221. The arrangement of beam splitters is in a polygonal pattern. In each case, the transfer leg is reflective, with the beam splitter being a dichroic mirror which is inclined at an angle of 11.25° to perpendicular, i.e. a small angle, say between 5° and 20°. It has been found that this angle optimizes balance between reflection and transmission. On each bounce from a beam splitter, part of the beam called the "detector leg" is transmitted through the beam splitter toward one of the detectors. Detector 231 is associated with the transfer leg of beam splitter 221 while the detector 233 is associated with the detector leg from the same beam splitter. Detector 235 is associated with the detector leg coming through beam splitter 211 while detector 237 is associated with the detector leg through beam splitter 213. Detector 239 is associated with the detector leg through beam splitter 215 while detector 241 is associated with the transfer leg from beam splitter 215 and the detector leg through beam splitter 217. Correspondingly, the detector 243 is associated with the transfer leg from beam splitter 217 and the detector leg through beam splitter 219. Each of the beam splitters is a dichroic mirror having different wavelength characteristics for decimating the input beam 202 into different colors which register at the different detectors. Coatings applied to the dichroic mirrors account for reflection of some wavelengths and transmission of other wavelengths. Laser light of a particular frequency will stimulate fluorescent emission in generally known wavelength bands. Light in these bands is collected and passed through an optical fiber to a detector array, the detectors arranged in a polygonal pattern of greater circumference than the polygonal pattern of beam splitters. Within each cluster decimation of the light occurs, with passbands of 10–75 nanometers registering at each detector, depending on the sharpness of filtering of the coatings applied to the beam splitters. Additional selectivity of the signals reaching the detector may be gained by a series of filters 251, 253, 255, 257, 259, 261 and 263, the filters arranged in a polygonal pattern with a polygonal circumference greater than the circumference of the beam splitters but less than the circumference of the detectors. Each of these filters is placed in front of a corresponding detector. The filter has a bandpass over a range of wavelengths which is of particular interest in the corresponding detector. Associated with each detector is a focusing lens 265 for focusing light in a detector leg on a sensitive spot of the detector. Each lens 265 is movable for adjusting the focal spot during calibration of the instrument.

In FIG. 7, a cluster with an array of detectors and an array of beam splitters is seen to be held in place by a frame 200 which generally supports detectors 237, 241, 233, 235, 239, 243 and 231 in a polygonal array where the polygon is drawn connecting the axial centers of each of the cylindrical detectors, the detectors being photomultiplier tubes. Each tube is seated in a tube mount 245. A tube connector base 247 makes contact with pins of each tube. An electrical feed-through 249 allows power to come to connector base 247 while signals exit the tube through another feed-through 251. Similar connector bases and feed-throughs exists for each tube. Within the center of the frame 200 is a coverplate 250. About a first close distance from the coverplate is a polygonal array of dichroic mirror holders for the dichroic mirrors 213, 217, 221, 211, 215 and 219. A slightly further distance are the filter holders 263, 261, 259, 257, 255, 253 and 251. The dichroic mirror holders and the filter holders are mounted in vertically removable housings so that dichroic mirrors and associated filters may be interchanged or replaced.

In FIG. 8, a plurality of clusters 301, 303 and 305 is shown to be vertically mounted on a rack 307 by means of standoff supports 311, 313 and 315. The standoff supports are merely illustrative of the manner in which three arrays may be mounted on a rail or rack for easy replacement or modular supplementation. Each cluster is of the type shown in FIG. 7.

In FIGS. 9–11, the construction of a removable beam splitter holder is shown. The beam splitter mirror 321 is held in a mirror holder frame 323 at a desired angle. Frame 323 is supported by a block 325 having channels for finger contact in a non-slip manner. The mirror holder frame 323 has a flat side 328 which presses against the flat side 327 of a seating block 329 having a central aperture 331 corresponding to the position of mirror 321. A facing block 339 has an aperture 341 in alignment with aperture 331 and with mirror 321. The flat side 327 is a reference surface for positioning of the mirror 321. A wire spring 343 serves to push the mirror holder frame 323 against the block 329.

FIGS. 12–14 show how the transmitted leg of a beam 361 may impinge upon the focusing lens 265. With motion of the focusing lens 265, as shown in FIG. 13 in the direction of the arrow C, the focused beam 362 is moved to a more sensitive spot 364 on the photomultiplier tube 231 in comparison to a less sensitive location 365 shown in FIG. 12. Additional sensitivity may be gained by slightly rotating the photomultiplier tube 231 with its housing, within the support frame to optimize the output signal for a particular detector leg 361 focused on a detection element in the photomultiplier tube. Motion is indicated by the arrows D.

FIG. 15 shows the construction of light collector 111 in FIG. 2. A flow cell 103 is shown at the left of the drawing with flow channel 109 and input fluid from fluidic system 105 passing through channel 109. As has been previously noted, a flow system is but one type of optical instrument where fluorescence can be observed. Non-flow systems may also be employed with the detection apparatus of the present invention. A large numerical aperture ("N.A.") lens system, i.e. N.A. greater than one, positioned as shown in FIG. 4 is described according to the lens data contained in the following table. The numbered optical surfaces in the figure correspond to surface numbers in the leftmost column of the table. All radii and thickness values are in millimeters. Surface curvature tolerances for the lens data include 5 fringes for power (deviation of actual curvature from nominal curvature) and 1 fringe for irregularity (deviation from a perfect spherical surface). Tilt tolerance is 0.05 degrees from normal in any direction. Material tolerances are 0.0005 for refractive index and 0.8% for Abbe number.

| Surface | Radius of Curvature | Thickness | Thickness Tolerance | Aperture Radius | Clear Aperture Radius | Material |
|---|---|---|---|---|---|---|
| 109 | 4 | 0.0889 | — | 0.2 | | Water |
| 301 | 4 | 1.94 | — | 4.6 | | Silica |
| 302 | 4 | 0.1682 | — | 4.6 | | Gel |
| 303 | 4 | 0.8 | .025 | 5.1 | 4.6 | BK7 |
| 304 | 4 | 3.915 | .025 | 4.6 | 4.6 | BK7 |
| 305 | −4.66 | 1.5 | .025 | 4.6A | 4.6 | Air |
| 306 | −16.918 | 5 | .05 | 8.5 | 7.3 | BK7 |
| 307 | −10.894 | 1 | .025 | 10 | 8.8 | Air |
| 308 | −26.836 | 5 | .10 | 11.5 | 10.2 | BK7 |
| 309 | −15.008 | 1 | .025 | 12.5 | 11.1 | Air |
| 310 | −103.704 | 9 | .10 | 13 | 11.9 | BK7 |
| 311 | −14.012 | 3 | .10 | 13 | 12.2 | SF8 |
| 312 | −34.38 | 2 | .05 | 15.5 | 14.1 | Air |
| 313 | +123.446 | 3 | .10 | 17 | 14.9 | SF8 |
| 314 | +34.38 | 12 | .10 | 17 | 15.1 | BK7 |
| 315 | −36.554 | 126.731 | .50 | 17 | 15.5 | Air |

The lens proper (surfaces 303 through 315) in this system is adapted to magnify and view cellular material within a cytometry flow cell or cuvette 103 (the flow cell inner and outer wall surfaces being optical surfaces 301 and 302 above). As indicated in the table, a flow cell has 0.007 inch (0.1778 mm) interior dimensions (wall-to-wall) and the fluorescent targets 109 to be detected and analyzed are immersed in saline water flowing through the cell 103, nominally for lens design purposes through the center of the cell a distance of 0.0889 mm from the cell's inner wall. The 1.94 mm thick, fused silica, planar cell wall has a refractive index$_{nD}$ of 1.45857 and an Abbe number$_{vD}$ of 67.7. An optical gel layer provides an interface between the cytometry flow cell and the lens proper and improves lens mounting tolerances. The gel material is preferably NyoGel OC-431A sold by William F. Nye, Inc. of New Bedford, Mass., and has refractive indices at the 0.40 µm, 0.55 µm and 0.70 µm principal lens design wavelengths, respectively, of 1.487, 1.467, and 1.459. The gel should have a thickness less than 0.5 mm, and is selected in the above design to be 0.1682 mm thick. Other cytometry flow cells with different interior and wall dimensions, and other optical gels or oils could be used, with appropriate modifications in the lens specifications, optimized using commercially available software. Although lens positioning tolerances would be much tighter (0.025 mm or less), the lens could also be integrated with or mounted to the flow cell without using optical gel.

The lens glass types BK7 and SF8 (Schott glass designations) have been selected because they are relatively inexpensive stock materials that are easy to obtain in quantity, and because they are easy to grind and polish and don't stain easily. Other glass types could be used instead, including similar glass types from other optical glass suppliers, with appropriate modifications in the lens specifications. The optical glass designated BK7 [517642] has a refractive index$_{nD}$ of 1.51680 and an Abbe number$_{vD}$ of 64.17, and the optical glass designated SF8 [689312] has a refractive index$_{nD}$ of 1.68893 and an Abbe number$_{vD}$ of 31.18. All of the lenses in the preferred embodiment have spherical surfaces because they are inexpensive, more readily available in bulk, are more alignment tolerant, and are easier to assemble and test than aspheric lenses. However, if desired, modified lens specifications using one or more aspheric lenses have lower on-axis aberrations and could be used, although from a commercial standpoint the performance improvement likely would not be sufficient to justify their significantly greater expense and assembly difficulty.

The basic lens requirements include a numerical aperture of at least 1.17. (An object N.A. of 1.20±0.01 was used in obtaining the preferred embodiment that is set forth in the table above. A numerical aperture of 1.20 provides about 10 to 15% greater light collection than one of 1.17) The field of view should be at least 200 µm diameter and, if possible, as much as 400 µm or better. The present preferred embodiment has a field of view of 400 µm diameter. The working distance should be at least 1.75 mm, (2.2 mm is achieved in the preferred embodiment.) Most importantly, a lens system of less optical aberrations and high image quality is required for better resolution compared to existing cytometry lenses. In particular, the RMS spot size (a measure of resolution) in image space (for hypothetical point objects) for all wavelengths and all field points should be at most 100 µm. The present preferred embodiment achieves a calculated geometrical spot size of 85.04 µm at full field and of 71.86 µm on-axis. This puts a minimum of 80% of the optical energy of the image of an infinitely small point source within a circle of less than 200 µm diameter. This is a significant improvement over one existing cytometry lens design's 442.6 µm full field and 365.2 µm on-axis spot sizes and 800 µm diameter circle energy (at 80% energy).

Other design parameters for the lens optimization software include a magnification of at least 10×, and preferably between 10.5× and 11.5×, and a back focal length of 127±2 mm (as seen for surface 15 in the table, a back focal length of 126.731 mm is obtained for the present embodiment), and a wavelength range at least from 400 mm to 700 mm (the entire visible light range). The total length and lens barrel diameter should be as small as possible, i.e. less than 57 mm and 41 mm respectively, since space near the flow cell is in high demand in cytometry instruments. A lens length of 47.2 mm (combined thickness for surfaces 3 to 14) and a maximum aperture radius (for less surfaces 13 to 15) of 17 mm show that these size goals have been met.

The lens is seen to comprise (a) a nearly hemispheric plano-convex crown glass lens (surface 308 through 305 in the above table including the cemented plate of identical material added for handling) with its planar side 303 closest to the cytometry flow cell and its convex surface 305 having a radius of curvature in a range from 3.5 to 5.5 mm (4.66 mm in the present preferred embodiment); (b) a pair of positive meniscus lenses (surfaces 306 to 309) with their concave sides 306 and 308 closest to the flow cell (i.e. on the object side of the lens system) and with the surfaces 308 and 309 of the second meniscus lens being less sharply curved than the corresponding surfaces 306 and 307 of the first meniscus lens, which are in turn less sharply curved than the convex surface 305 of the plano-convex lens; and (c) a pair of positive doublet lens elements (surfaces 310–315) to compensate for chromatic aberrations from the first three lens elements. The near hemispheric shape of the plano-convex lens (total axial thickness of the lens plus the attached plate of identical crown glass material being 4.715 mm compared to the 4.66 mm radius of curvature of the convex surface 305, of difference of less than 1.2%) gives the lens system its large field of view. The convex radius of curvature range provides for a long working distance of at least 1.75 mm (about 2.2 mm in the present embodiment). Use of two meniscus lenses, and also the use of crown glass material (refractive index less then 1.55) for both the meniscus lenses and the plano-convex lens, reduce aberrations, which are generally proportional to the square of the amount of light bending at each refractive surface. The lower aberrations provide improved resolution, as indicated above the image spot size and circle energy. The doublets are not achromats themselves, but are over compensated so that the chromatic aberrations are reduced for the entire lens system.

What is claimed is:

1. A detector apparatus for analyzing light emitted from a fluorescent material, wherein the light is collected by a light collector and formed into an output beam for analysis, comprising
a means for collimating said output beam, the collimated output beam having a projected optical axis,
a plurality of dichroic mirrors disposed along the projected optical axis in a manner separating light at each mirror into a reflected beam and a transmitted beam, wherein, at each mirror, one of the reflected and transmitted beams is a transfer leg carrying the beam further to the next dichroic mirror and the other is a leg carrying light to a detector, wherein a majority of the dichroic mirrors receives light from a reflected beam coming from another dichroic mirror.

2. The apparatus of claim 1 wherein all of the dichroic mirrors except one receive light from a reflected beam coming from a dichroic mirror.

3. The apparatus of claim 1 wherein the number of dichroic mirrors is at least four.

4. The apparatus of claim 1, wherein a plurality of dichroic mirrors are angled relative to an optical axis of the transfer leg or the output beam at an angle of 20° or less.

5. The apparatus of claim 1, wherein a plurality of dichroic mirrors are angled relative to an optical axis of the transfer leg or the output beam at an angle between 5° and 20°.

6. The apparatus of claim 1, wherein a plurality of dichroic mirrors are angled relative to an optical axis of the transfer leg or the output beam at an angle of about 11.25°.

7. The apparatus of claim 1 wherein said detectors are arranged in a polygonal pattern having a first circumference and said dichroic mirrors are arranged in a polygonal pattern having a second circumference smaller than said first circumference.

8. The apparatus of claim 7, further comprising a plurality of filters arranged in a polygonal pattern having a third circumference, wherein a filter is associated with each detector and said third circumference is greater than said second circumference but less than said first circumference.

9. The apparatus of claim 1 wherein said dichroic mirrors are arranged such that said transfer legs carrying said beam from one dichroic mirror further to the next dichroic mirror follow a zigzag pattern.

10. The apparatus of claim 1 wherein said means for collimating said output beam receives light by means of an optical fiber.

11. The apparatus of claim 1, wherein said detectors are photomultiplier tubes or semiconductors.

* * * * *